United States Patent [19]
Dalyea

[11] Patent Number: 5,823,977
[45] Date of Patent: Oct. 20, 1998

[54] WATERPROOF PROTECTIVE COVERING FOR MEDICAL USES

[76] Inventor: Lorraine Dalyea, 132 S. Carr Dr. #7, Glendale, Calif. 91205

[21] Appl. No.: 816,571

[22] Filed: Mar. 13, 1997

[51] Int. Cl.⁶ .................................................. A61F 13/00
[52] U.S. Cl. ................................................. 602/3; 602/79
[58] Field of Search ................................. 602/3, 41–59, 602/78, 79; 604/179, 174, 177, 180; 128/888, 889

[56] References Cited

U.S. PATENT DOCUMENTS

| | | | |
|---|---|---|---|
| 3,270,742 | 9/1966 | Costa | 602/79 |
| 4,513,739 | 4/1985 | Johns | 602/53 |
| 5,662,598 | 9/1997 | Tobin | 602/53 X |

*Primary Examiner*—Linda C. Dvorak
*Assistant Examiner*—Kim M. Lee

[57] ABSTRACT

A new Waterproof Protective Covering For Medical Uses for covering an intravenous needle site, surgical suture site, a cast or a bandage that needs to be protected from moisture. The inventive device includes generally of a flexible plastic which includes elastic on two sides and a sealing section on the other two sides.

8 Claims, 3 Drawing Sheets

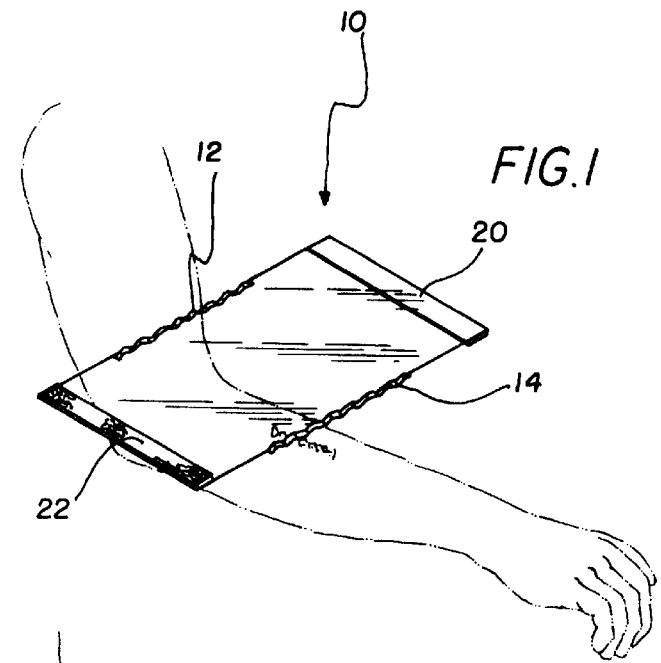
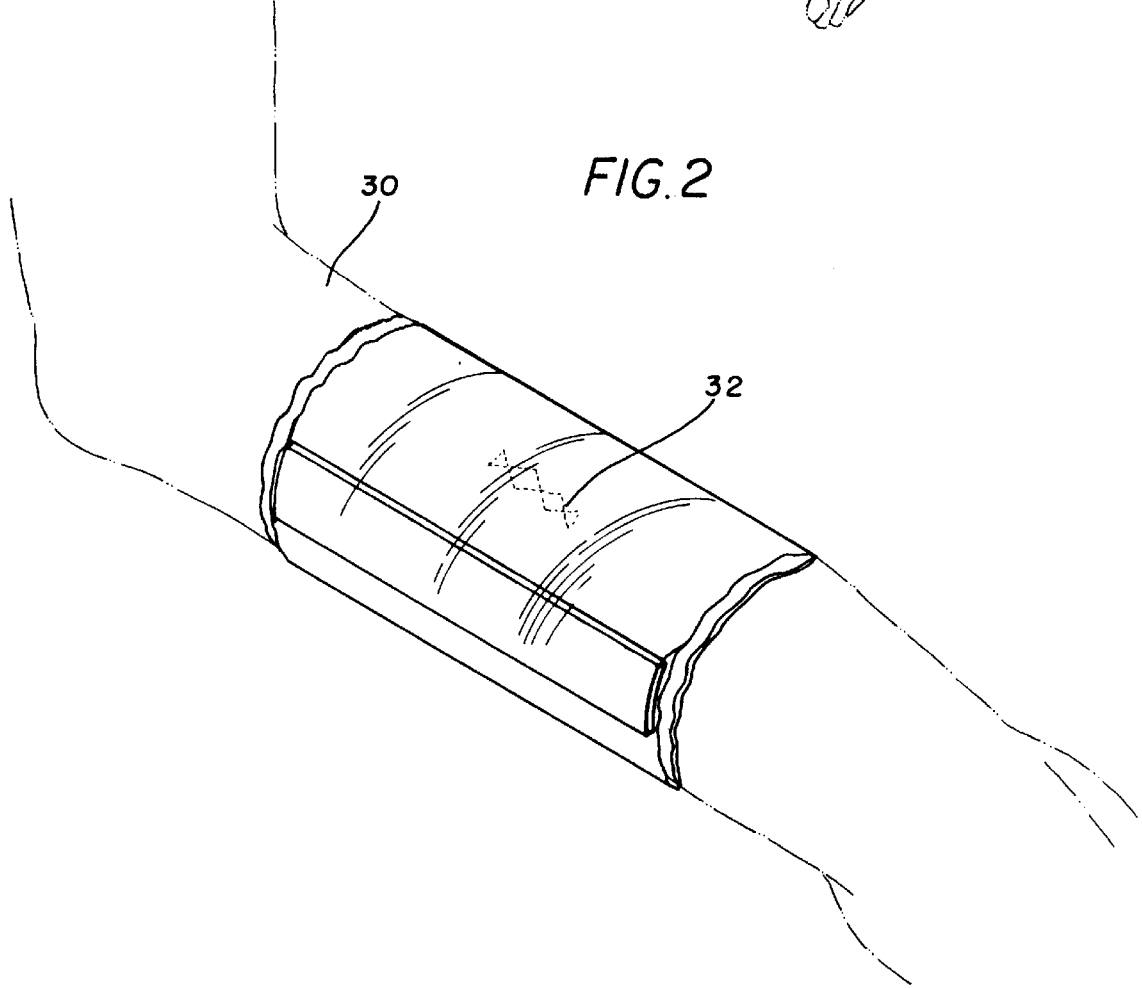

WATERPROOF PROTECTIVE COVERING FOR MEDICAL USES

BACKGROUND OF THE INVENTION

1. Field of the Invention

The present invention relates to waterproof coverings and more particularly pertains to a new Waterproof Protective Covering For Medical Uses for covering an intravenous needle site, surgical suture site, a cast or a bandage that needs to be protected from moisture.

2. Description of the Prior Art

The use of waterproof coverings is known in the prior art. More specifically, waterproof coverings heretofore devised and utilized are known to consist basically of familiar, expected and obvious structural configurations, notwithstanding the myriad of designs encompassed by the crowded prior art which have been developed for the fulfillment of countless objectives and requirements.

Known prior art waterproof coverings include U.S. Pat. No. 4,562,834; U.S. Pat. No. 5,342,286; U.S. Pat. No. 4,727,864; U.S. Pat. No. 4,523,586; U.S. Pat. No. 4,768,501 and U.S. Pat. No. 4,911,151.

While these devices fulfill their respective, particular objectives and requirements, the aforementioned patents do not disclose a new Waterproof Protective Covering For Medical Uses. The inventive device includes generally a flexible plastic which includes elastic on two sides and a sealing means on another two sides.

In these respects, the Waterproof Protective Covering For Medical Uses according to the present invention substantially departs from the conventional concepts and designs of the prior art, and in so doing provides an apparatus primarily developed for the purpose of covering an intravenous needle site, surgical suture site, a cast or a bandage that needs to be protected from moisture.

SUMMARY OF THE INVENTION

In view of the foregoing disadvantages inherent in the known types of waterproof coverings now present in the prior art, the present invention provides a new Waterproof Protective Covering For Medical Uses construction wherein the same can be utilized for covering an intravenous needle site, surgical suture site, a cast or a bandage that needs to be protected from moisture.

The general purpose of the present invention, which will be described subsequently in greater detail, is to provide a new Waterproof Protective Covering For Medical Uses apparatus and method which has many of the advantages of the waterproof coverings mentioned heretofore and many novel features that result in a new Waterproof Protective Covering For Medical Uses which is not anticipated, rendered obvious, suggested, or even implied by any of the prior art waterproof coverings, either alone or in any combination thereof.

To attain this, the present invention generally comprises generally of a flexible plastic which includes elastic on two sides and a sealing means on another two sides.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Waterproof Protective Covering For Medical Uses apparatus and method which has many of the advantages of the waterproof coverings mentioned heretofore and many novel features that result in a new Waterproof Protective Covering For Medical Uses which is not anticipated, rendered obvious, suggested, or even implied by any of the prior art waterproof coverings, either alone or in any combination thereof.

It is another object of the present invention to provide a new Waterproof Protective Covering For Medical Uses which may be easily and efficiently manufactured and marketed.

It is a further object of the present invention to provide a new Waterproof Protective Covering For Medical Uses which is of a durable and reliable construction.

An even further object of the present invention is to provide a new Waterproof Protective Covering For Medical Uses which is susceptible of a low cost of manufacture with regard to both materials and labor, and which accordingly is then susceptible of low prices of sale to the consuming public, thereby making such Waterproof Protective Covering For Medical Uses economically available to the buying public.

Still yet another object of the present invention is to provide a new Waterproof Protective Covering For Medical Uses which provides in the apparatuses and methods of the prior art some of the advantages thereof, while simultaneously overcoming some of the disadvantages normally associated therewith.

Still another object of the present invention is to provide a new Waterproof Protective Covering For Medical Uses for covering an intravenous needle site, surgical suture site, a cast or a bandage that needs to be protected from moisture.

Yet another object of the present invention is to provide a new Waterproof Protective Covering For Medical Uses which includes generally of a flexible plastic which includes elastic on two sides and a sealing means on another two sides.

Still yet another object of the present invention is to provide a new Waterproof Protective Covering For Medical Uses that provides a safe way to have a bath or other moisture induced activities while keeping a specific area dry.

Even still another object of the present invention is to provide a new Waterproof Protective Covering For Medical Uses that prevents dirt from causing an infection.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a side view of a new Waterproof Protective Covering For Medical Uses according to the present invention.

FIG. 2 is the present invention in use on an arm.

DESCRIPTION OF THE PREFERRED EMBODIMENT

Figure 3:
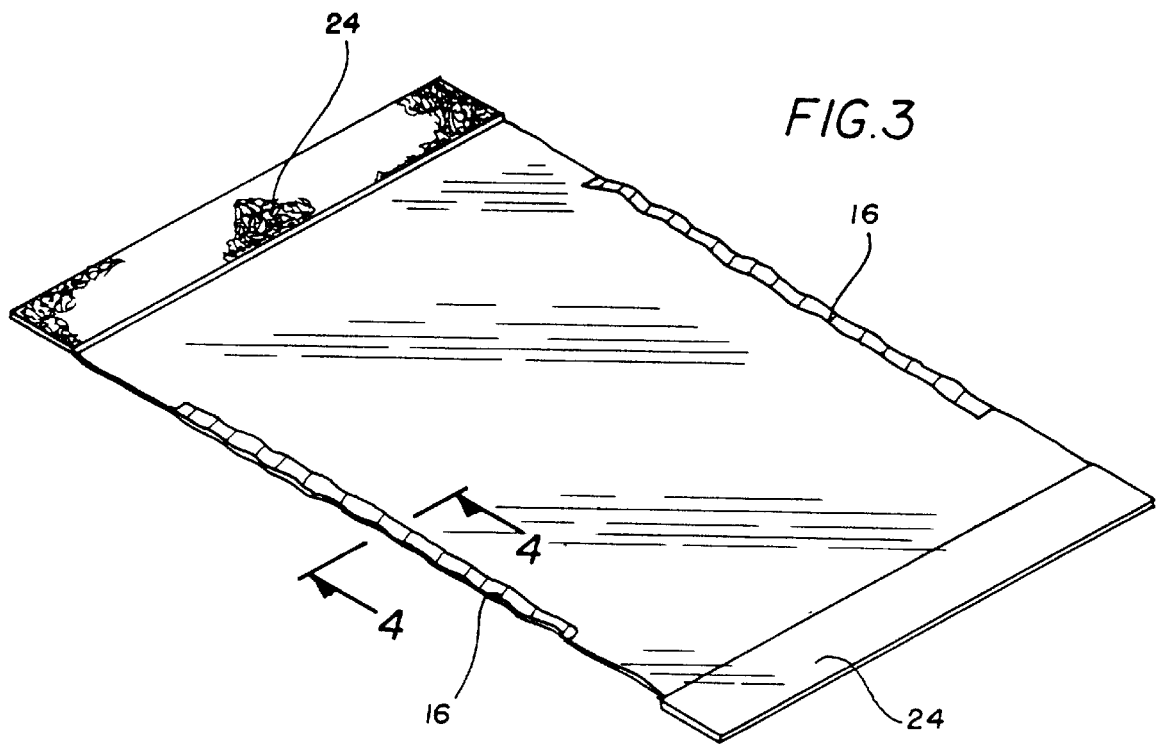
FIG. 3 is a side view of the underside of the present invention.
Figure 4:
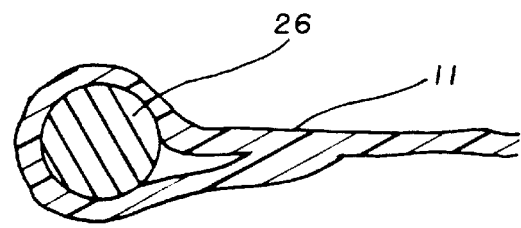
FIG. 4 is a cross-sectional view taken along line 4—4 of FIG. 3.
Figure 5:
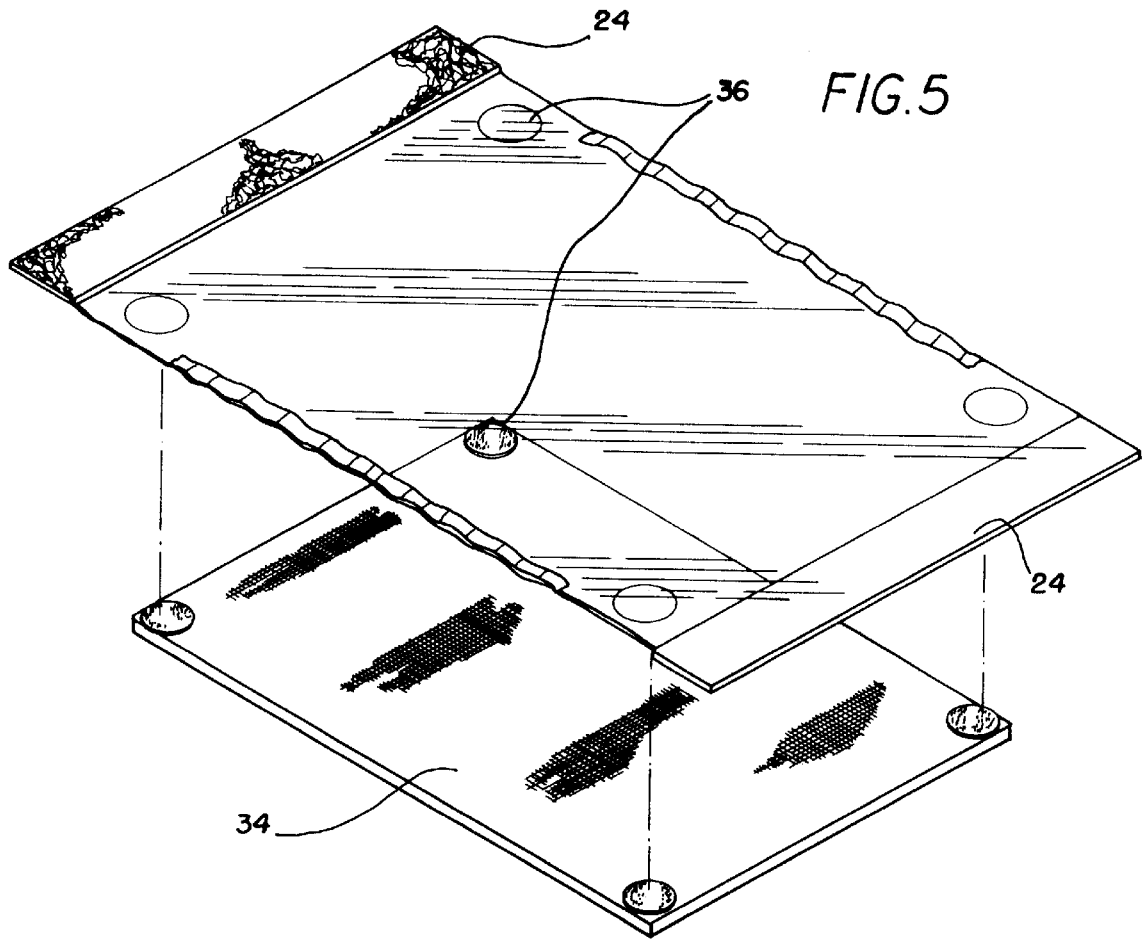
FIG. 5 is an exploded isometric view of the present invention.
Figure 6:
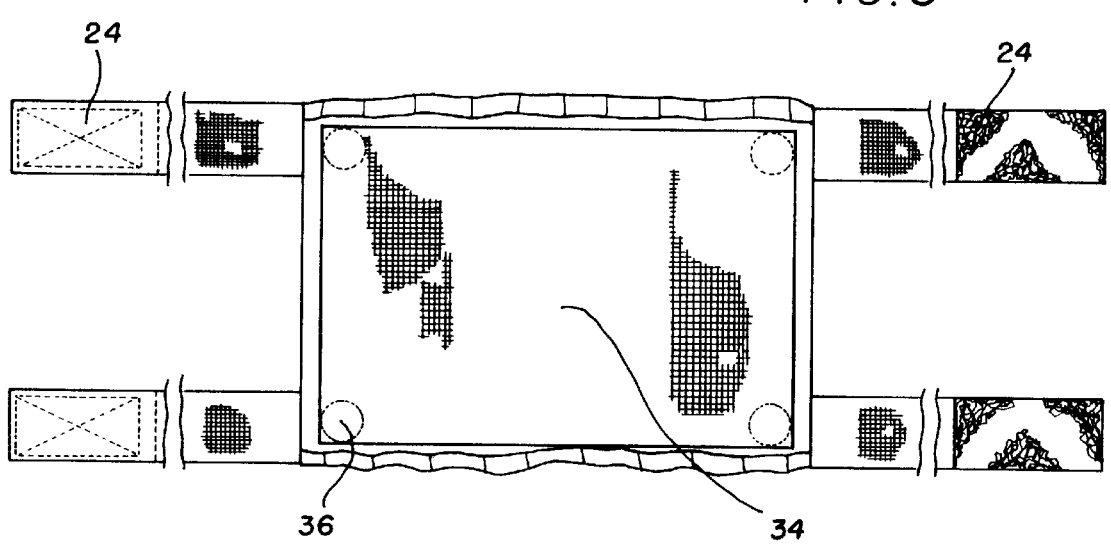
FIG. 6 is an bottom view of the present invention.

With reference now to the drawings, and in particular to FIGS. 1 through 6 thereof, a new Waterproof Protective Covering For Medical Uses embodying the principles and concepts of the present invention and generally designated by the reference numeral 10 will be described.

More specifically, it will be noted that the Waterproof Protective Covering For Medical Uses 10 comprises generally of a flexible plastic which includes elastic on two sides and a sealing means on another two sides.

As best illustrated in FIGS. 1 through 6, it can be shown that the present invention teaches Waterproof Protective Covering that is novel and nonobvious and fulfills a need in the industry.

The present invention comprises A Waterproof Protective Covering For Medical Uses 10. The covering 10 includes a flat four sided, flexible, plastic material 11. The plastic material 11 used in the present invention is preferably suited for biological purposes and could be biodegradable to protect the environment. The covering 11 should be waterproof covering. The waterproof covering 11 includes elastic 16 on a first and a second side 12 & 14 and a sealing means 24 on a third 20 and a fourth side 22.

The covering 11 forms a rectangular shaped section. The rectangular section measures about 12 inches long and about 6 inches wide. The covering 11 further comprises on an underside 28 a four sided gauze material 34. The gauze 34 is removably attached to the plastic covering 11 by using at least four portions of a sealing means 36. The sealing means 24 can include but are not limited to fasteners such as VELCRO ®. The sealing means 24 are formed on a first side 14 and a second side 16. The sealing means 24 forms a strip extending laterally across said first end 14 and said second end 16.

In use, the present invention, can be applied by placing the covering gently over the affected area, wrapping the covering snugly around the area without creating any undue discomfort and closing the covering with the sealing means.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A waterproof protective covering for fastening to a user to protect a wound or a bandage, the waterproof protective covering comprising:

a flexible waterproof covering member having a pair of opposing sides, said flexible covering member further having a pair of opposing ends, a pair of elastic members, one of said elastic members appended to each of the respective opposing sides;

a pair of fastening means being adapted for securing the waterproof covering member around the wound or the bandage;

said pair of fastening means being positioned proximate said opposing ends; and a coupling means for coupling a gauze member to an underside of the flexible covering;

wherein the coupling means includes hook and loop fasteners comprising hook portions and loop portions, wherein one of the portions of said hook and loop fasteners is attached to the underside of the flexible covering member and the other of the portions of said hook and loop fasteners is attached to said gauze member; and wherein each of the portions of said hook and loop fasteners is positioned proximate a respective corner of said gauze member.

2. The waterproof protective covering of claim 9, wherein the covering member forms a rectangle.

3. The waterproof protective covering of claim 2, wherein the rectangle measures about 12 inches long and about 6 inches wide.

4. The waterproof protective covering of claim 1 further comprising:

a coupling means for coupling a gauze member to an underside of the flexible covering.

5. The waterproof protective covering of claim 4 wherein the coupling means includes four pairs of hook and loop fasteners wherein within each of said pairs of hook and loop fasteners one of a hook portion and a loop portion is attached to the underside of the flexible covering member and the other of the hook portion and the loop portion is attached to the gauze member.

6. The waterproof protective covering of claim 5 wherein each of said pairs of hook and loop fasteners is positioned proximate a respective corner of said gauze member.

7. The waterproof protective covering of claim 1 wherein the fastening means comprises:

two pairs of fastening tabs, one pair of fastening tabs at each of said opposing ends;

one of said pair of fastening tabs including one of a tab hook portion and a tab loop portion, the other of said pair of fastening tabs including the other of said tab hook portion and said tab loop portion;

wherein said tab hook portion and said tab loop portion are positioned such that one can engage the other when said protective covering is fastened to said user.

8. A waterproof protective covering for fastening to a user to protect a wound or a bandage, the waterproof protective covering comprising:

a substantially rectangular flexible waterproof covering member having a pair of opposing sides, said flexible covering member further having a pair of opposing ends;

a pair of elastic members, one of said elastic members appended to each of the respective opposing sides;

a pair of fastening means being adapted for securing the waterproof covering member around the wound or the bandage;

wherein said pair of fastening means includes two pairs of fastening tabs, one pair of fastening tabs at each of said opposing ends;

one of said pair of fastening tabs including one of a tab hook portion and a tab loop portion, the other of said pair of fastening tabs including the other of said tab hook portion and said tab loop portion;

wherein said tab hook portion and said tab loop portion are positioned such that one can engage the other when said protective covering is fastened to said user;

said pair of fastening means being positioned proximate said opposing ends;

a coupling means for coupling a gauze member to an underside of the flexible covering;

wherein the coupling means includes four pairs of hook an loop fasteners wherein within each of said pairs of hook and loop fasteners one of a hook portion and a loop portion is attached to the underside of the flexible covering member and the other of the hook portion and the loop portion is attached to the gauze member; and wherein each of said pairs of hook and loop fasteners is positioned proximate a respective corner of said gauze member.

* * * * *